United States Patent [19]

Ullman et al.

[11] Patent Number: 5,137,808
[45] Date of Patent: * Aug. 11, 1992

[54] IMMUNOASSAY DEVICE

[75] Inventors: Edwin F. Ullman, Atherton; Pyare Khanna, Fremont; Rohan Peries, Palo Alto, all of Calif.

[73] Assignee: Syntex (U.S.A.) Inc., Palo Alto, Calif.

[ * ] Notice: The portion of the term of this patent subsequent to Aug. 15, 2006 has been disclaimed.

[21] Appl. No.: 388,176

[22] Filed: Jul. 31, 1989

Related U.S. Application Data

[63] Continuation of Ser. No. 35,562, Apr. 7, 1987, Pat. No. 4,857,453.

[51] Int. Cl.$^5$ ............................................. G01N 33/53
[52] U.S. Cl. ..................................... 435/7.9; 435/7.92; 435/975; 422/56; 422/58; 436/514; 436/807; 436/810
[58] Field of Search .................. 435/7, 805, 810; 436/807, 810, 514; 422/56, 58

[56] References Cited

U.S. PATENT DOCUMENTS 4,857,453 0/0000 Ullman et al. ............... 435/7
4,918,025 4/1990 Grenner ...................... 436/165

OTHER PUBLICATIONS

USPQ 228, Studiengesellschaft Kohle mbH V. Northern Petrochemical Co., pp. 837–845.

Primary Examiner—Christine Nucker
Attorney, Agent, or Firm—Theodore J. Leitereq; Mark L. Bosse

[57] ABSTRACT

A device is disclosed for conducting an assay method. The device comprises a housing, means enclosed in the housing for capturing a member of a specific binding pair in a zone and for allowing liquid to be transported by capillary action away from the zone, one or more self-contained liquid reagents enclosed in the housing for conducting an assay method for the determination of an analyte in the sample, and means in the housing for introducing the sample into the device. Preferably, the self-contained reagents are liquid reagents which are contained in a breakable container. The device of the invention finds use in assay methods for the determination of an analyte in a sample suspected of containing the analyte. Kits for conducting an assay method are also disclosed.

70 Claims, 3 Drawing Sheets

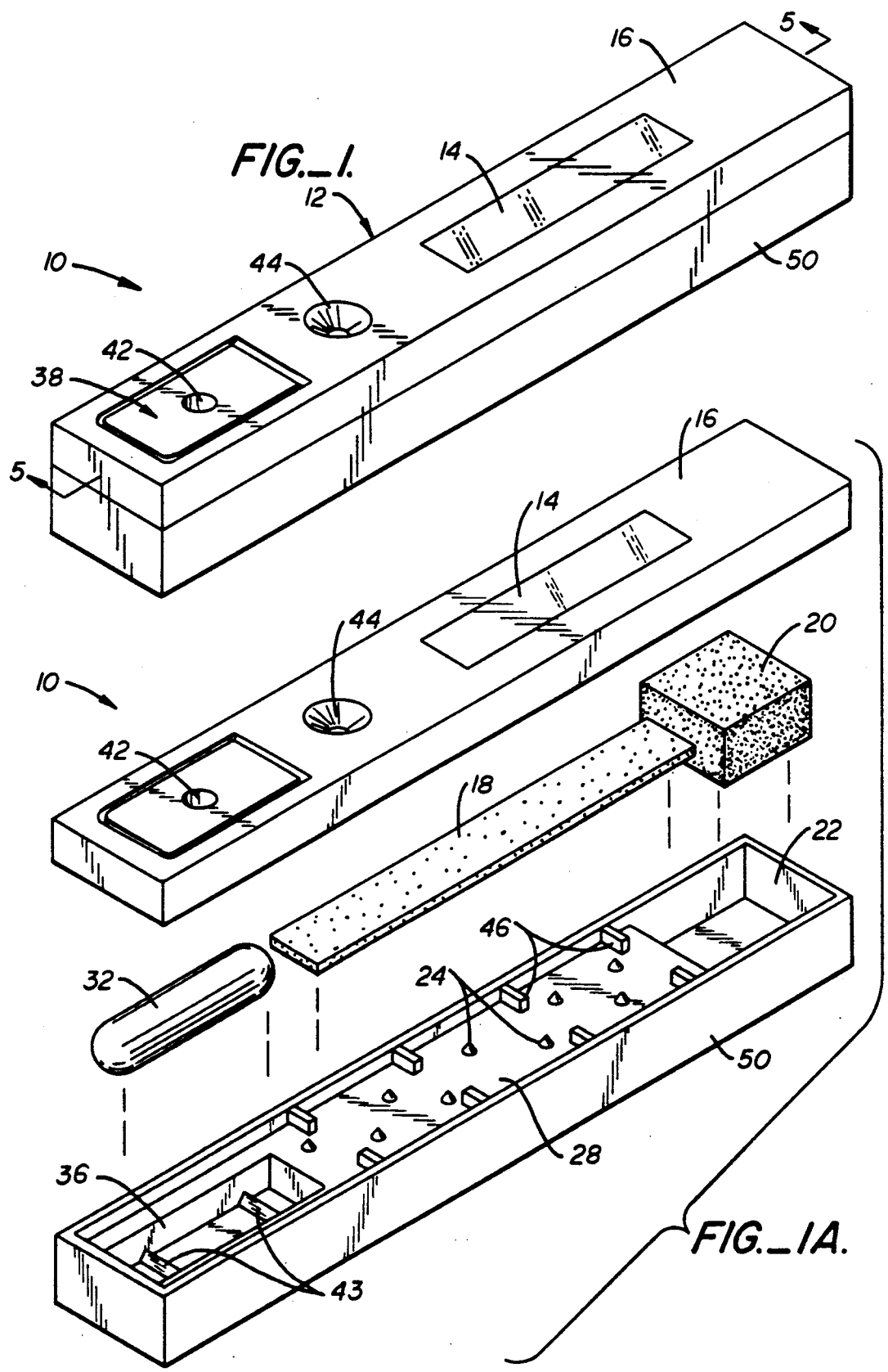

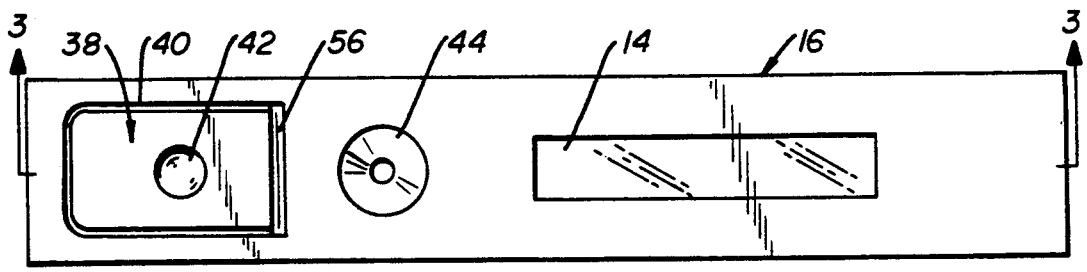
FIG._2.
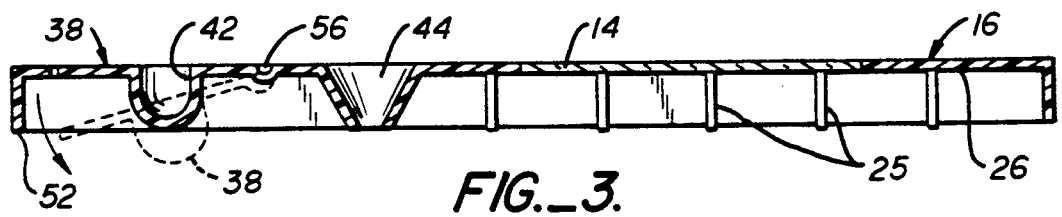
FIG._3.
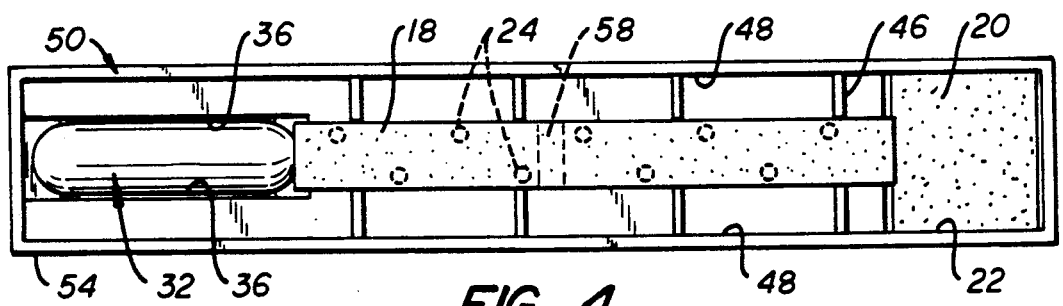
FIG._4.
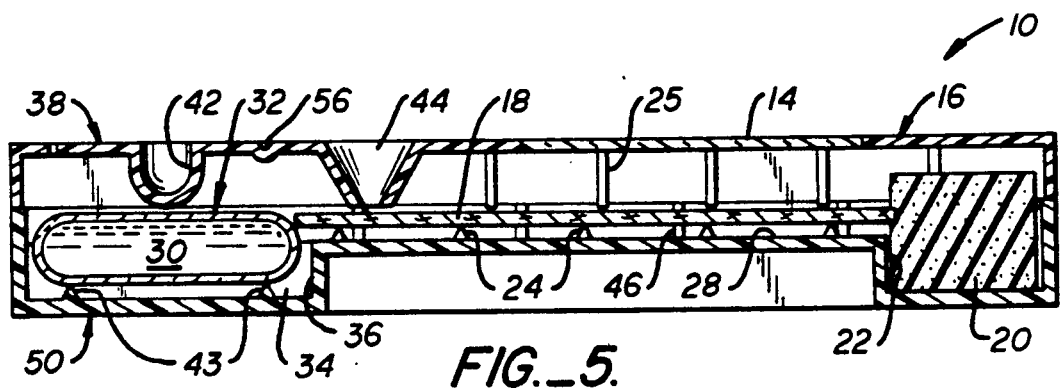
FIG._5.

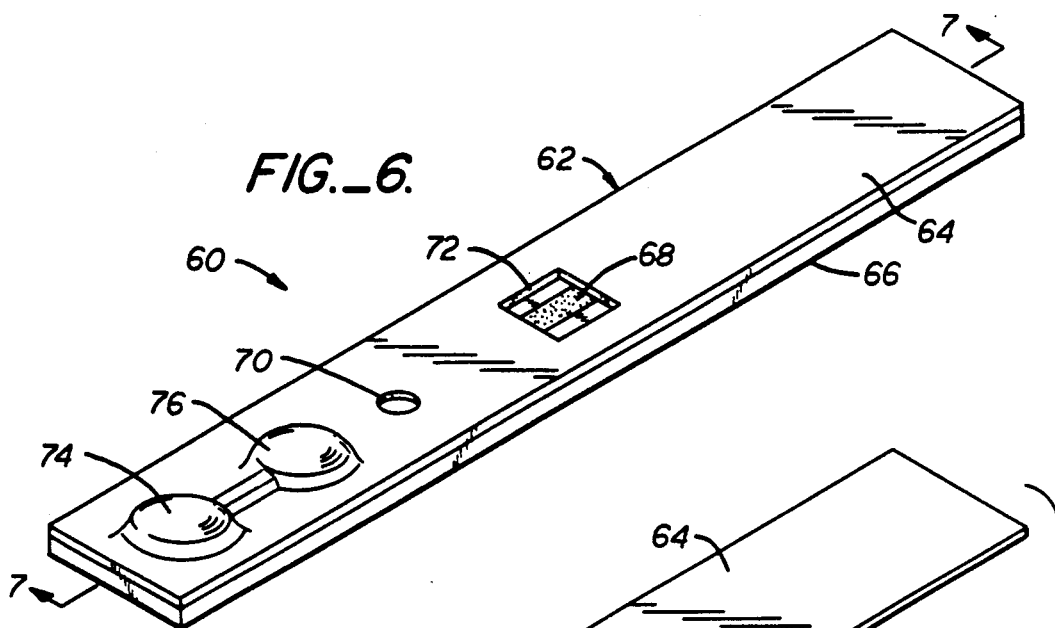
FIG._6.
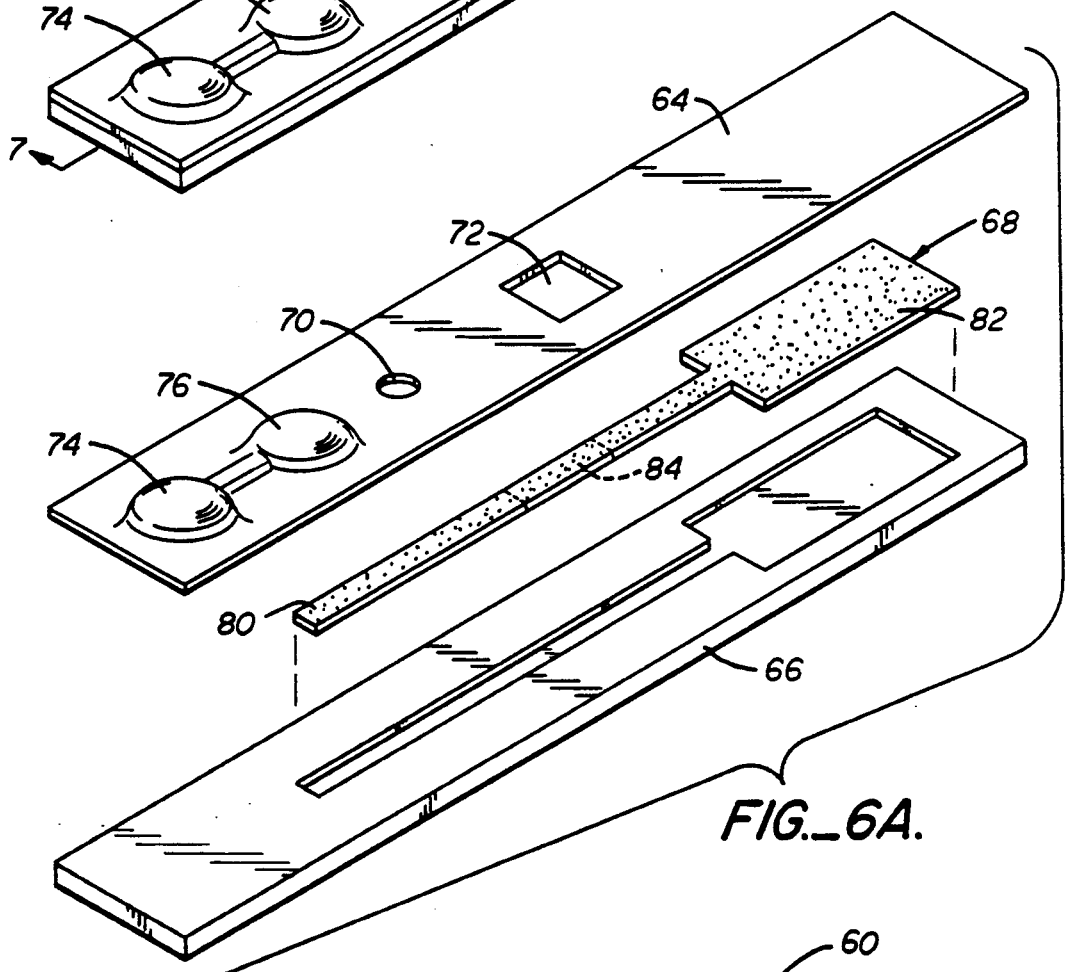
FIG._6A.
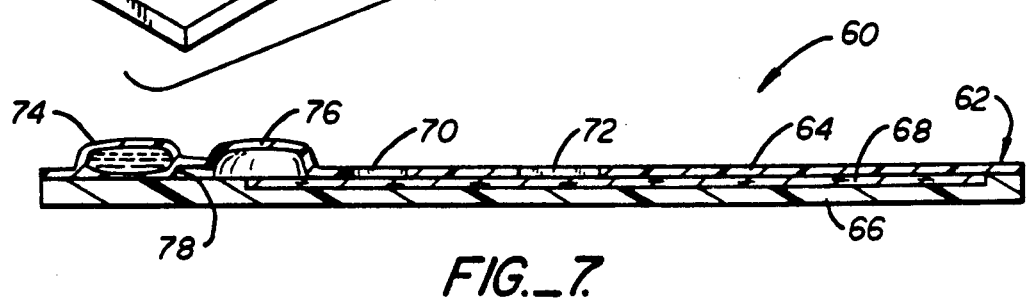
FIG._7.

IMMUNOASSAY DEVICE

This is a continuation of pending application Ser. No. 07/035,562, filed Apr. 7, 1987, now U.S. Pat. No. 4,857,453.

BACKGROUND OF THE INVENTION

1. Field of the Invention

This invention relates to devices for conducting assay methods. The ability to employ receptors directed to specific compounds in assaying for the presence of a compound of interest has created a burgeoning diagnostic assay business. Over the years, numerous simplified test systems have been developed for the rapid detection of materials of interest in biological and industrial fluids. These systems or devices in their simplest form usually involve the combination of a test reagent specifically reactable with the material of interest to give a visual response and a carrier for the test reagent. Bibulous paper is the most commonly used material for the carrier. A portion of the carrier is usually impregnated or coated with one or more of the test reagents. The portion of the carrier containing the test reagents is brought into contact with the sample containing the material of interest. The contact may be accomplished by immersing the portion of the carrier with the test reagents into the sample in an aqueous medium or an aqueous sample can be allowed to traverse a bibulous carrier by capillary migration through the portin of the carrier containing the test reagent. The test zone may be first created on the carrier or the zone may be produced during the running of the assay.

A concentrating zone method in heterogeneous assays has found broad application. The method employs a device that has an immunosorbing zone to which a specific binding pair member is fixed non-diffusively. The immunosorbing zone serves as an entry for the sample and reagent solutions. In liquid receiving relationship, either directly or indirectly with the immunosorbing zone, is a liquid absorbing zone which serves to draw liquid through the immunosorbing zone, store liquid and may serve to control the rate at which the liquid is drawn through the immunosorbing zone. Employed in the method in conjunction with the device is a signal producing system which has a signal label member conjugated to a specific binding pair member. The immunosorbing zone may include one or more members of the signal producing system which are bound to the zone in a manner to permit or inhibit diffusive movement of the signal producing system component. In accordance with the method protocol, the amount of signal label bound in the detection zone in the immunosorbing zone is related to the amount of the material of interest in the sample. In the method the assay device is contacted with liquid sample to which may have been added one or more components of the signal producing system. The device may subsequently be contacted with one or more solutions which contain remaining components of the signal producing system and serve to wash the immunosorbing zone free of nonspecifically bound signal label. The signal producing system provides for a detectible signal in the immunosorbing zone which can be compared to a signal level based on a standard having a known amount of analyte.

The concentrating zone method technology has been applied in a number of commercial products, such as, for example, the ICON ® device (Hybritech Corporation), the TESTPACK TM device (Abbott Laboratories), and the SUDS TM device (Murex Corporation).

A chromatographic technique for carrying out qualitative and/or quantitative assays for an analyte are also known. The assay involves contacting a portion of a bibulous material with a liquid medium containing the analyte and optionally other members of a signal producing system, which includes a labeled specific binding pair member. The bibulous material usually contains one or more zones for specifically binding the analyte. The bibulous material may also contain one or more members of a signal producing system. The liquid medium is allowed to traverse the bibulous material by capillary action and the bibulous material is contacted with remaining members of the signal producing system. The presence of analyte in a sample can be determined by examining the bibulous material for a signal in each of the zones and the quantity of analyte can be determined by relating the position of a border between signal and no signal in any one zone to the amount of analyte in the sample or counting the number of zones having or not having a signal and relating the number of zones to the amount of analyte in the sample. Exemplary of an immunochromotographic technique in accordance with the first approach above is the Acculevel TM product sold by Syva Company.

It is desirable to provide an immunoassay with the broad application of a heterogeneous assay which is also simple, rapid, accurate, and safe for unskilled persons to perform in environments outside of sophisticated laboratory settings. It is also desirable to provide a diagnostic device for conducting such assays wherein all of the reagents are contained and it is left only to add the sample to be tested to the device. Such a device would be convenient and eliminate the need for critical addition steps.

2. Description of the Related Art

A concentrating zone method in heterogeneous immunoassays is described in U.S. Pat. No. 4,366,241. A test device for detecting low concentrations of substances in fluids is described in U.S. Pat. No. 3,811,840. An improved heterogeneous immunoassay method and assembly is discussed in European Application Publication No. 0 141 547. U.S. Pat. No. 4,517,288 discloses a solid phase system for ligand assay. An integrated material for chemical analysis and a method of using the same is discussed in U.S. Pat. No. 4,270,920. The performance of routine chemical reactions in compartmentalized containers is described in U.S. Pat. No. 3,825,410. An immunodiffusion plate apparatus is described in U.S. Pat. No. 3,645,687. The performance of chemical or biological reactions within an absorbent matrix pad is discussed in U.S. Pat. No. 3,888,629. A test device for assaying liquid samples for the presence of a predetermined reagent is described in U.S. Pat. No. 4,246,339. An immobilized antibody or antigen for immunoassay is disclosed in U.S. Pat. No. 4,407,943. U.S. Pat. No. 3,915,647 discloses a device for determining the concentration of a substance in a fluid. U.S. Pat. No. 4,632,901 describes a method and apparatus for immuno-assays.

SUMMARY OF THE INVENTION

The invention described herein is a device for conducting an assay method. The device comprises a housing, means enclosed in the housing for capturing a member of a specific binding pair in a zone and for allowing liquid to be transported by capillary action away from the zone. One or more self-contained liquid reagents are enclosed in the housing. The reagents are those utilized in conducting an assay method for the determination of an analyte in a sample. The housing is also provided with means for introducing a sample into the device. Preferably, the self-contained reagents are liquid reagents which are contained in a breakable container. The device of the invention finds use in assay methods for the determination of an analyte in a sample suspected of containing the analyte. The invention further includes kits for conducting an assay. The device of the present invention is a compact reagent delivery system devised for convenient on site qualitative testing of a variety of analytes.

DESCRIPTION OF THE DRAWING

FIG. 1 is a top perspective view taken slightly from the side of a device in accordance with the present invention.

FIG. 1A is an exploded view of the device of FIG. 1.

FIG. 2 is a top plan view of the device of FIG. 1.

FIG. 3 is a cross-sectional view of the top half of device of FIG. 1 taken along lines 3—3.

FIG. 4 is a top view of the bottom half of the device of FIG. 1.

FIG. 5 is a cross-sectional view of the device of FIG. 1 taken along lines 5—5.

FIG. 6 is a top perspective view taken slightly from the side of another embodiment of the device of the present invention.

FIG. 6A is an exploded view of the device of FIG. 6.

FIG. 7 is a cross-sectional view of the device of FIG. 6 taken along lines 7—7.

DESCRIPTION OF THE SPECIFIC EMBODIMENTS

One aspect of the present invention concerns a device for conducting an assay method. The device comprises a housing and means enclosed in the housing for capturing a member of a specific binding pair in a zone and for allowing liquid to be transported by capillary action away from the zone. One or more self-contained reagents are enclosed in the housing for conducting an assay method for the determination of an analyte in the sample. The housing further includes means for introducing the sample into the device. Preferably, the self-contained reagents are liquid reagents which are contained in a breakable container. The device of the invention finds use in assay methods for the determination of an analyte in a sample suspecting of containing the analyte.

The device of the present invention has broad application. The device may be utilized in any number of assays wherein absorbent material is utilized to assist the flow of liquid away from a contact portion where the absorbent material is contacted with a medium containing the analyte to be determined or reagents for analyzing for the analyte. The device of the present invention is simple to use, normally requiring merely introducing the sample in liquid form into the device and manipulating the device to release the self-contained reagents therein. Thus, the device of the present invention greatly assists in reducing operator associated errors.

Before proceeding further with the description of the specific embodiments of the present invention, a number of terms will be defined.

Analyte—the compound or composition to be measured that is capable of binding specifically to an antibody, usually an antigen or drug.

The precise nature of the antigenic and drug analytes together with numerous examples thereof are disclosed in U.S. Pat. No. 4,299,916 to Litman, et al., particularly columns 16 to 23, and in U.S. Pat. No. 4,275,149, columns 17 and 18, the disclosures of which are incorporated herein by reference.

The analytes are characterized by having single binding sites (monovalent) or multiple binding sites (polyvalent). The polyvalent analytes will normally be poly(amino acids), i.e., polypeptides and proteins, polysaccharides, nucleic acids, and combinations thereof. Such combinations or assemblages include bacteria, viruses, chromosomes, genes, mitochondria, nuclei, cell membranes, and the like.

A wide variety of proteins may be considered as to the family of proteins having similar structural features, proteins having particular biological functions, proteins related to specific microorganisms, particularly disease causing microorganisms, etc. Exemplary of microbiological analytes are lipsopolysaccharides, proteins and nucleic acids from organisms such as chlamydia, herpes virus, hepatitis virus (A, B, or non-A, non-B), gonorrhea, T. pallidum, and the like.

The following are classes of proteins related by sructure: protamines, histones, albumins, globulins, scleroproteins, phosphoproteins, mucoproteins, chromoproteins, lipoproteins, nucleoproteins, glycolproteins, proteoglycans, unclassified proteins, e.g. somatotrophin, prolactin, insulin, pepsin.

A number of proteins found in human plasma are important clinically and include: prealbumin, albumin, $\alpha_1$-lipoprotein, $\alpha_1$-acid glycoprotein, $\alpha_1$-antitrypsin, $\alpha_1$-glycoprotein, transcortin, 4.6S-postalbumin, tryptophan-poor $\alpha_1$-glycoprotein, $\alpha_1$X-glycoprotein, thyroxin-binding globulin, inter-$\alpha$-trypsin-inhibitor, Gc-globulin, haptoglobulin, ceruloplasmin, cholinesterase, $\alpha_2$-lipoprotein(s), myoglobin, C-reactive Protein, $\alpha_2$-macroglobulin, $\alpha_2$-HS-glycoprotein, Zn-$\alpha_2$-glycoprotein, $\alpha_2$-neuramino-glycoprotein, erythropoietin, $\beta$-lipoprotein, transferrin, hemopexin, fibrinogen, plasminogen, $\beta_2$-glycoprotein I, $\beta_2$-glycoprotein II.

Complement factors and blood clotting factors are examplary of analytes. Important protein hormones such as Parathyroid hormone, Thyrocalcitonin, Insulin, Glucagon, Relaxin, Erythropoietin, Melanotropin, Somatotropin, Corticotropin, Thyrotropin, Follicle-stimulating hormone, Luteinizing hormone, Luteomammotropic hormone, Gonadotropin (chorionic gonadotropin);

Tissue Hormones such as secretin, gastrin, angiotensin I and II, bradykinin, human placental lactogen are exemplary of analytes.

Peptide Hormones from the Neurohypophysis such as oxytocin, vasopressin, releasing factors (RF) CRF, LRF, TRF, somatotropin-RF, GRF, FSH-RF, PIF, MIF are exemplary of analytes.

The monoepitopic ligand analytes will generally be from about 100 to 2,000 molecular weight, more usually from 125 to 1,000 molecular weight. The analytes of interest include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which include cocaine and benzoyl ecgonine, their derivatives and metabolites, ergot alkaloids, which include the diethylamide of lysergic acid; steroid alkaloids; iminazoyl alkaloids; quinazoline alkaloids, isoquinoline alkaloids; quinoline alkaloids, which include quinine and quinidine; diterpene alkaloids, their derivatives and metabolites.

The next group of drugs includes steroids, which includes the estrogens, estrogens, androgens, andreocortical steroids, bile acids, cardiotonic glycosides and glycones, which includes digoxin and digoxigenin, saponins and sapogenins, their derivatives and metabolites. Also included are the steroid mimetic substances, such as diethylstilbestrol.

The next group of drugs is lactams having from 5 to 6 annular or ring members, which include the barbiturates, e.g. phenobarbital and secobarbital, diphenylhydantonin, primidone, ethosuximide, and their metabolites.

The next group of drugs is aminoalkylbenzenes, with alkyl of from 2 to 3 carbon atoms, which includes the amphetamines, catecholamines, which includes ephedrine, L-dopa, epinephrine, narcine, papaverine, and their metabolites.

The next group of drugs is benzheterocyclics which include oxazepam, chlorpromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes the vitamins such as A, B, e.g., $B_{12}$, C, D, E and K, folic acid, and thiamine.

The next group of drugs is prostaglandins, which differ by the degree and sites of hydroxylation and unsaturation.

The next group of drugs is antibiotics, which include penicillin, chloromycetin, actinomycetin, tetracycline, terramycin, the metabolites and derivatives.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, amitriptyline, nortriptyline, lidocaine, procaineamide, acetylprocaineamide, propranolol, griseofulvin, valproic acid, butyrophenones, antihistamines, antichlolinergic drugs, such as atropine, their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfenamides, their metabolites and derivatives.

For receptor analytes, the molecular weights will generally range from 10,000 to $2 \times 10^8$, more usually from 10,000 to $10^6$. For immunoglobulins, IgA, IgG, IgE and IgM, the molecular weights will generally vary from about 160,000 to about $10^6$. Enzymes will normally range from about 10,000 to 1,000,000 in molecular weight. Natural receptors vary widely, generally being at least about 25,000 molecular weight and may be $10^6$ or higher molecular weight, including such materials as avidin, DNA, RNA, thyroxine binding globulin, thyroxine binding prealbumin, transcortin, etc.

Member of a specific binding pair ("sbp member")—one of two different molecules having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair such as antigen-antibody, although other specific binding pairs such as biotin-avidin hormones-hormone receptors, nucleic acid duplexes, IgG-protein A, DNA-DNA, DNA-RNA, and the like are not immunological pairs but are included in the definition.

Ligand—any organic compound for which a receptor naturally exists or can be prepared.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acid, protein A, complement component Clq. and the like.

Labeled sbp member—a label, generally capable of electrochemical detection or absorption or emission of electromagnetic radiation, a catalyst, frequently an enzyme, bound to a first sbp member. The labeled sbp member is a member of the signal producing system and the first sbp member is chosen to bind to the second sbp member in accordance with a particular protocol in an assay.

Antibody—an immunoglobulin, or derivative or fragmeent thereof, having an area in the surface or in a cavity which specifically binds to and is thereby defined as complementary with a particular spatial and polar organization of another molecule. The antibody can be monoclonal or polyclonal and can be prepared by techniques that are well known in the art such as, for example, immunization of a host and collection of sera or hybrid cell line technology.

Antibody for the analyte—an antibody specific for an analyte.

Bibulous metarial—a porous material having pores of at least $0.1\mu$, preferably at least $1.0\mu$, which is susceptible to traversal by an aqueous medium in response to capillary force. Such materials are generally hydrophilic or are capable of being rendered hydrophilic and include inorganic powders such as silica, magnesium sulfate, and alumina; natural polymer materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, etc.; either used by thermselves or in conjunction with other materials; ceramic materials; and the like. The bibulous material can be attached to a support. On the other hand, the bibulous material may provide its own support. The bibulous material may be polyfunctional or be capable or being polyfunctionalized to permit covalent bonding of receptors or antibodies as well as to permit bonding of other compounds which form a part of the signal producing system.

Binding of receptors and antibodies to the bibulous material may be accomplished by well-known techniques, commonly available in the literature. See, for example, "Immobilized Enzymes," Ichiro Chibata, Halsted Press, New York (1978) and Cuatrecasas, *J. Bio. Chem.*, 245:3059 (1970).

The piece of bibulous material can be a single structure such as a sheet cut into strips or it can be several strips or particulate material bound to a support or solid surface such as found, for example, in thin-layer chromatography and may have an absorbent pad either as an integral part or in liquid contact. The piece of bibulous material can also be a sheet having lanes thereon, capable of spotting to induce lane formation, wherein a spearate assay can be conducted in each lane. The piece of bibolous material can have a rectangular, circular, oval, triagonal or other shape provided that there is at least one direction of traversal of a test solution by capillary migration. Other directions of traversal may occur such as in an oval or circular piece contacted in the center with the test solution. However, the main consideration is that there be at least one direction of flow to a predetermined site. In the following discussion strips of bibulous material will be described by way of illustration and not limitation.

The support for the bibulous material, where a support is desired or necessary, will normally be water insoluble, non-porous, and rigid and usually will be of the same length and width as the bibuolous strip but may be larger or smaller. A wide variety of organic and inorganic materials, both natural and synthetic, and combinations thereof, may be employed provided only that the support does not interfere with the capillary action of the bibulous materials, or non-specifically bind assay components, or interfere with the signal producing system. Illustrative polymers include polyethylene, polypropylene, poly(4-methylbutene), polystyrene, polymethacrylate, poly(ethylene terephthalate), nylon, poly(vinyl butyrate), glass, ceramics, metals, and the like.

Label—A label may be any molecule bound to an sbp member that is required to produce a signal. In the subject invention, the label may be inert and serve solely as a binding site for a member of the signal producing means or it may spontaneously produce a detectable signal or may produce a detectable signal in conjunction with a signal producing means. The label may be isotopic or nonisotopic, preferably non isotopic. However, an isotopic label can be preferred for achieving high sensitivity when using radio-autographic detections with photographic film.

Signal producing means—means capable of interacting with the label to produce a detectible signal. Such means include, for example, electromagnetic radiation, heat, chemical reagents, and the like. Where chemical reagents are employed, some of the chemical reagents can be included as part of a developer solution. The chemical reagents can include substrates, coenzymes, enhancers, enhancers, second enzymes, activators, cofactors, inhibitors, scavengers, metal ions, specific binding substances required for binding of signal generating substances, and the like. Some of the chemical reagents such as coenzymes, substances that react with enzymic products, other enzymes and catalysts, and the like can be bound to the bibulous material.

Signal producing system—The signal producing system may have one or more components, at least one component being a labeled spb member. The signal producing system includes all of the reagents required to produce a measurable signal including signal producing means capable of interacting with the label to produce a signal.

The signal producing system provides a signal detectable by external means, normally by measurement of electromagnetic radiation, desirably by visual examination. For the most part, the signal producing system includes a chromophoric substrate and enzyme, where chromophoric substrates are enzymatically converted to dyes which absorb light in the ultraviolet or visible region, phosphors or fluorescers.

The signal producing system can include at least one catalyst as a label, usually at least one enzyme, and at least one substrate and may include two or more catalysts and a plurality of substrates, and may include a combination of enzymes, where the substrate of one enzyme is the product of the other enzyme. The operation of the signal producing system is to produce a product which provides a detectable signal at the predetermined site, related to the presence of label at the predetermined site.

Two catalysts may be employed, either a combination of an enzyme and a non-enzyme catalyst or two enzymes, where the two catalysts are related in that the product of one is the substrate of the other. In this system, there need be only one substrate which can undergo successive changes catalyzed by the catalysts, which results in the compound involved with production of a detectable signal. For the most part, however, there wil normally be a substrate for the first enzyme in the series and a second compound, which serves as a precursor to the compound involved in the production of the signal, normally providing the compound which produces the signal. Thus, the product of the first enzyme may react with the precursor to the compound that produces a signal to provide the compounds that generates the signal.

Where two enzymes are employed, the involved reactions will be, for the most part, hydrolysis or redox reactions. In the case of hydrolysis, a derivatized dye precursor that has a hydrolytically labile bond, the hydrolytic enzyme and an enzyme that catalyzes the released dye precursors to a dye conversion product is illustrative of this type of system. In redox reactions, a first enzyme can produce an essential oxidizing substrate required for the second enzyme, where the second enzyme catalyzes the reaction between the oxidizing substrate and a dye precursor.

Where two enzymes are used, the first enzymatic reaction may involve hydrolytic cleavage or a redox reaction of the substrate to provide a product which is the substrate of another enzyme. The first situation may be illustrated by glucose-6-phosphate being catalytically hydrolyzed by alkaline phosphatase to glucose, where glucose is a substrate for glucose oxidase. The second situation may be illustrated by glucose being oxidized by glucose oxidase to provide hydrogen peroxide which would enzymatically react with a leuco dye to produce a signal generator.

Coupled catalysts can also involve an enzyme with a non-enzymatic catalyst. The enzyme can produce a reactant which undergoes a reaction catalyzed by the non-enzymatic catalyst or the non-enzymatic catalyst may produce a substrate (includes coenzymes) for the enzyme. A wide variety of non-enzymatic catalysts which may be employed are found in U.S. Pat. No. 4,160,645, issued Jul. 10, 1979, the appropriate protions of which are incorporated herein by reference.

Various combinations of enyzmes may be employed to provide a signal generating compound. Particularly, combinations of hydrolases may be employed to produce an insoluble signal generator. Alternatively, combinations of hydrolases and oxidoreductases can provide the signal generating compound. Also, combinations of oxidoreductases may be used to produce an insoluble signal generating compound.

For combinations of enzymes one enzyme can be non-diffusively bound to the bibulous material, while the other enzyme is the label conjugated to the analyte. Additionally, one or more other members of the signal producing system can be bound to the bibulous material depending on the particular signal producing system chosen or the particular protocol followed.

To order to have a detectable signal, it is desirable to provide means for amplifying the signal produced by the presence of the label at the predetermined site. Therefore, it will usually be preferable for the label to be a catalyst or luminescent compound or radioisotope, most preferably a catalyst. Preferably, catalysts are enzymes and coenzymes which can produce a multiplicity of signal generating molecules from a single label.

An enzyme or coenzyme is employed which provides the desired amplification by producing a product, which absorbs light, e.g., a dye, or emits light upon irradiation, e.g., a fluorescer. Alternatively, the catalytic reaction can lead to direct light emission, e.g., chemiluminescence. A large number of enzymes and coenzymes for providing such products are indicated in U.S. Pat. No. 4,275,149 bridging columns 19 to 23, and U.S. Pat. No. 4,318,980, columns 10 to 14, which disclosures are incorporated herein by reference.

A number of enzyme combinations are set forth in U.S. Pat. No. 4,275,149, bridging columns 23 to 28, which combinations can find use in the subject invention. This disclosure is incorporated herein by reference.

Of particular interest are enzymes which involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horse radish peroxidase, lactoperoxidase, or microperoxidase. Additional enzyme combinations may be found in the subject matter incorporated by reference. When a single enzyme is used as a label, other enzymes may find use such as hydrolases, transferases, and oxidoreductases, preferably, hydrolases such as alkaline phosphatase and β-galactosidase. Alternatively luciferases may be used such as firefly luciferase and bacterial luciferase.

Illustrative coenzymes which find use include NAD[H]; NADP[H], pyridoxal phosphate; FAD[H]; FMN[H], etc., usually coenzymes involving cycling reactions, see particularly U.S. Pat. No. 4,318,980.

The product of the enzyme reaction will usually be a dye or fluorescer. A large number of illustrative fluorescers are indicated in U.S. Pat. No. 4,275,149, columns 30 and 31, which disclosure is incorporated herein by reference.

Ancillary materials—Various ancillary materials will frequently be employed in the assay in accordance with the present invention. For example, buffers will normally be present in the assay medium, as well as stabilizers. Frequently, in addition to these additives, additional proteins may be included, such as albumins, or surfactants, particularly, non-ionic surfactants, binding enhancers, e.g. polyalkylene glycols, or the like.

Immunoconcentrating assembly—the immunoconcentrating assembly generally has an immunosorbing zone and a liquid absorbing zone. The immunosorbing zone and the liquid absorbing zone are usually engaged in a liquid receiving relationship either directly or indirectly. The immunoconcentrating assembly can include one or more immunosorbing zones. The immunosorbing zone and the liquid absorbing zone can form one integral unit such as a strip having one or more immunosorbing zones. Alternatively, the immunosorbing zone and the liquid absorbing zone can be distinct. For example, the immunosorbing zone may be a membrane to which an sbp member is attached. The liquid absorbing zone can be absorbent material in the form of a strip, pad, plug, wick, or the like, in liquid receiving relationship with the immunosorbing zone. The liquid absorbent material can be of any hydrophilic bibulous material such as paper, sponge, felt, porous polymers and the like.

Immunosorbing zone—a bibulous solid film, layer or sheet, frequently in contact with or a portion of the piece of bibulous material, to which a sbp member is non-diffusively bound. Immunosorbing zone frequently has a small fluid capacity as compared to the total assay device capacity. One or more members of a signal producing system may be bound directly or indirectly to the immunosorbing zone. The immunosorbing zone has a specific binding capability for a complementary sbp member.

Liquid absorbing zone—a bibulous solid material either directly or indirectly in liquid receiving relationship with the immunosorbing zone and acting as a reservoir or storage zone capable of a storing a substantially greater liquid volume than the immunosorbing zone. The liquid absorbing zone acts as a pump to pump liquid through and out of the immunosorbing zone. The liquid absorbing zone serves to control the volume of the fluid that traverses the immunosorbing zone. A further function for the liquid absorbing zone may be to measure the amount of liquid which is passed through the device. By providing for graduations at sequential positions extending away from the immunosorbing zone and along the liquid absorbing zone, one can determine when the solvent front is at a certain position. One can provide for dyes which will become colored upon dissolution or contact with a solvent front to provide an indication that the solvent has traversed the device.

Self-contained liquid reagent(s)—one or more liquid reagents for conducting an assay confined for subsequent release during an assay method employing the device of the invention. The reagent is self-contained within the device of the present invention. The reagent can be an sbp member, a member of a signal producing system, an ancillary reagent, or the like and will be in liquid form, usually in an aqueous medium, confined in at least one breakable container in the device of the invention. The container can be integral with the housing of the present device or separate therefrom or both where more than one self-contained reagent is employed. Upon breaking the container(s) the reagent is rendered capable of traversing the bibulous material employed in the present assay device.

The containers will be water impermeable and may be rigid or flexible and capable of being broken by crushing, cutting, puncturing, melting, breaking a seal between such container and the housing of the device, and the like. Common materials include glass, plastics, waxes, polymer membranes, and the like. Normally the volume of a container will be at least the fluid absorption volume of the materials in the device but may be more or less. When less than the fluid absorption volume of the device more than one container will frequently be employed. Container volumes will usually be 0.1 to 15 mL, preferably 0.3 to 5 mL, but may be as little as 5 cubic microns as, for example, when the liquid is contained in numerous microcapsules. The continer can be of any shape compatible with the present device, e.g., ellipsoidal, rectangular, spherical, and so forth.

The device of the present invention will next be described in more detail with reference to the attached drawings. It should be emphasized that the following description is by way of illustration and not limitation. Various specific embodiments of the present invention will be suggested to those skilled in the art with the present description in mind. Such embodiments are intended to be within the scope of the present invention.

Referring now to FIG. 1 depicts device 10. The device comprises housing 12, which can be of any suitable shape or size in accordance with the particular type of assay to be conducted. Housing 12 can be fabricated from any suitable material appropriate for the type of assay being conducted. The material used to fabricate the housing should not interfere with the sample, the sample medium, or any reagents utilized in conducting the assay including members of the single producing system. Preferably, the housing is formed from a thermoplastic material, or the like. Generally, the housing has means 14 which will allow the immunosorbing zone or zones on the bibulous material to be visualized so that one may be able to determine the result of an assay. Accordingly, the top portion 16 of housing 12 can be constructed entirely of a clear thermoplastic material. Alternatively, only the area allowing for visualization of the immunosorbing zone or zones can be a clear material or such area can merely be an opening in the top portion of device 10. The dimensions of the housing again depend on the particular assay being conducted.

Device 10 further includes means enclosed in the housing for capturing a member of a specific binding pair in a zone and for allowing liquid to be transported by capillary action away from the zone. In the embodiment depicted in FIGS. 1-5 such means comprises a piece of bibulous material, a bibulous strip 18, having one or more immunosorbing zones. Preferably, the bibulous strip is non-removably confined in device 10. A liquid absorbent material 20 in liquid receiving relationship with bibulous strip 18 may optionally be included in device 10, preferably, non-removably confined in device 10. The combination of strip 18 and absorbent means 20 provides for capturing an sbp member in a zone and transporting liquid away from the zone by capillary action. Liquid absorbing member 20 is conveniently located in recess portion 22 of device 10. In the device of FIGS. 1-5 recess portion 22 is located at one end of device 10 opposite the end having means 42 for breaking container 32 containing the self contained liquid reagent (30). Such is by way of example only. Other embodiments will be suggested to those skilled in the art. For example, number 20 can be positioned near or remote from the means 44 for introducing the sample.

The inner walls of housing 12 can contain means 24 for supportively confining strip 18 in the housing. In some circumstances it is important that the front and back sides of strip 18 be free from contact with the inner walls of the housing so that the capillary action of the strip remains essentially unchanged. Furthermore, as the liquid traverses the strip, the strip expands.

Exemplary of means 24 are protruding elements 24 found on inner walls 26 and 28 of housing 12. Elements 24 are generally integral with the inner walls of housing 12 and may be in the form of posts which are conical, oblong, oval, rectangular, triangular, or the like. A key feature of elements 24 is that they minimize the contact area with strip 18 so that the capillarity of strip 18 is not altered in any significant manner. By the term "altering in any significant manner" is meant that the capillary action of strip 18 is not altered such that the performance of the immunochemical test is significantly affected thereby reducing or eliminating the accuracy of the test. For example, sufficient capillary action must be maintained in order to be able to accurately determine the analyte in a sample.

In FIGS. 2-5, elements 24 and 25 lie in rows parallel to the longitudinal sides of housing 12. Generally, elements 24 and 25 have dimensions such as to allow slight up and down movement of the strip in the housing in the dry state and to prevent such movement when the strip is wetted by the traversing liquid. Usually, the distance of such movement is 0 mm to 3.0 mm when the strip is in the dry state. Generally, on each of the top and bottom inner walls of housing 12, there are about from 2 to 15 elements 24 or 25, respectively, per side, having a length of about 0.5 to 4 mm each. In an alternative embodiment strip 18 can be affixed to a support, thus eliminating the need for elements 24 or 25 or both. Means 46 are provided to maintain strip 18 free from contact with the inner side walls 48 of the bottom portion 50 of device 10. Such means can take the form of elements 46 protruding from walls 48. The shape of elements 24, 25, and 46 can each independently or all be rectangular, oval, triangular, oblong, conical, or the like. In general means 46 serve the same function as means 24 and 25.

Liquid absorbing member 20 is confined in recessed area 22. Member 20 can be in intimate contact with the walls of the recessed portion 22 of the housing or the walls may also contain means for supportively confining liquid absorbing member 20. In any event member 20 is confined within recess 22 of housing 12 to be maintained in liquid receiving relationship with strip 18.

Further enclosed, preferably, non-removably, in housing 12 is self-contained liquid reagent 30 in breakable container 32. The liquid reagent is utilized in the determination of an analyte in the sample. The liquid reagent can include members of a signal producing system such as a labelled sbp member, and the like. Container 32 is located in recess 34 of device 10. Container 32 is conveniently manufactured from a breakable material such as glass, plastic, and the like. Container 32 is normally supportively confined within recess 34 by means 36 in such a manner that it is easily broken at the desired time. Means 36 is a wall or can take the form of a shoulder, rib, protrusion, or the like. Recess 34 can contain reagents for conducting an assay in dry form or diffusively bound to a support.

Housing 12 further includes means 38 for assisting in the breaking of container 32. Preferably, means 38 includes a movable portion 40 hinged at 56 generally lying over recessed area 34. Means 38 can be manipulated to break capsule 32. Furthermore, means 38 can also include button 42 lying opposite container 32. When movable portion 40 is depressed, button 42 is forced against container 32 and container 32 is broken. Members 43 can be included to assist breakage of 32.

Housing 12 further includes means 44 therein for introducing the sample into device 10. In the device pictured in FIGS. 1-5 means 44 is an opening through which sample can be deposited on strip 18. Such an opening can be utilized in any configuration or shape provided self-contained liquid reagents will not exit from device 10 after capsule 32 is broken. The opening can be cylindrical, conical, rectangular, square or the like. Alternatively, means 44 can take the form of a septum made out of an elastomeric material such as rubber, plastic, or the like.

Delivery may be made into device 10 by means of a dropper, syringe needle, or the like containing the sample to be analyzed. Generally, where the bibulous material is a strip, means 44 is located between the recessed area 34 and the location of absorbent member 20. Means 44 is located in a such a way that delivery of the sample into the device will result in the sample being deposited on strip 18. Other means for introducing the sample into the device will be suggested to those skilled in the art.

A preferred embodiment for assembly of the device of the present invention may be seen with reference to FIGS. 1-5. The present device is conveniently formed from two pieces herein referred to as top half or piece 16 and bottom half or piece 50. Pieces 16 and 50 are joined along edge lines 52 on piece 16 and 54 on piece 50. Conveniently, the two halves can include means for interlocking the halves. For example, top half 16 can contain a protrusion which is designed to snap fit with a protrusion receiving means on piece 50. After placing strip 18, absorbent member 20, and container 32 into piece 50, piece 16 and piece 50 are joined together along their edges. Piece 16 and pieced 50 may be sealed together to produce housing 12 by application of sonic energy, an adhesive, heat, or the like, according to conventional techniques. The preferred technique is the application of sonic energy to produce a sonic weld and the edge can be equipped with appropriate energy directors. The use of top and bottom pieces for assembly of the device of the invention is merely illustrative. Other means of forming the present device, depending on the particular configuration chosen for the device, will be suggested to those skilled in the art to having reference to the disclosure contained herein.

Top half 16 of device 10 can possess on its face a scale to assist in quantitating the amount of analyte in the sample. For example, where quantitation is the result of measuring the length within the immunosorbing zone in which detection of signal is observed, an indicating means such as a scale assists in obtaining the quantitative results.

Devices other than that depicted in FIG. 1-5 are included as part of this invention. For example, multiple means 44 for introducing sample, multiple containers 30, multiple means 38 for breaking the container and/or multiple visualization means 14 can be employed. Moreover a number of such devices can be assembled as a single device that is able to assay a number of samples.

Another embodiment of a device in accordance with the present invention is depicted in FIGS. 6 and 7. Device 60 comprises housing 62 generally comprising top piece 64, bottom piece 66, and bibulous piece 68. Top piece 64 has means 70 for introducing a sample into the device and means 72 for viewing at least a portion of bibulous piece 68 for the result of an assay. In the embodiment depicted both means are openings in piece 64. Device 60 includes two bubble containers 74 and 76 separated by breakable or rupturable seal 78. Containers 74 and 76 are formed by two raised areas on top piece 64 in conjunction with bottom piece 66. The material forming containers 74 and 76 can be the same as or different from that for the entire device or for top piece 64. Generally, containers 74 and 76 are fabricated of a flexible material such as plastic, rubber, or the like. Seal 78 can be formed between pieces 64 and 66 by heat, adhesive, or the like. The primary requirement for seal 78 is that it not permit liquid reagents in 76 to pass into 74 until seal 78 is ruptured by, for example, depressing container 76. On the other hand, seal 78 must rupture readily when container 76 is depressed.

Bottom piece 66 can be made of a material that is the same as or different from that of piece 64. Preferably, piece 66 is formed from a rigid material to provide an opposed rigid surface when container 76 is depressed. However, piece 66 could be fabricated from a non-rigid material and container 76 can be depressed between two fingers of the user or on a rigid surface.

Bibulous piece 68 comprises strip portion 80 that extends partially into container 74 and pad portion 82 opposite thereto. Generally, strip portion 80 has an immunosorbing zone 84, normally capable of being viewed in whole or in part through means 72. Device 60 can be fabricated by bringing together top piece 64 and bottom piece 66 with material 68 in the appropriate placement. Pieces 64 and 66 can be sealed together by heat, adhesive, sonic energy, or the like.

In the embodiment of FIGS. 6 and 7, container 76 contains a liquid reagent and container 74 is empty. Alternatively, additional containers can be included in the device separated by rupturable seals. The seals are ruptured either simultaneously or sequentially when it is desired to utilize the liquid reagents in the assay to be conducted. Mixing of one or more liquid reagents after rupture of the seals can be achieved, for example, by flexing the flexible container.

The solvent for the sample to be analyzed and the solvent for the self-contained reagents will normally be an aqueous medium, which may be up to about 40 weight percent of other polar solvents, particularly oxygenated solvents of from 1 to 6, more usually of from 1 to 4 carbon atoms, including alcohols, ethers and the like. Usually, the cosolvents will be present in less than about 20 weight percent. Under some circumstances depending on the nature of the sample, some or all of the aqueous medium could be provided by the sample itself.

The pH for the medium will usually be in the range of 4-11, more usually 5-10, and preferably in the range of about 6-9. The pH is chosen to maintain a significant site of binding affinity of the binding members and optimal generation of signal by the signal producing system. Various buffers may be used to achieve the desired pH and maintain the pH during the assay. Illustrative buffers include borate, phosphate, carbonate, tris, barbital and the like. The particular buffer employed is not critical, but in individual assays, one buffer may be preferred over another.

Desirably, from about 0.05 to 0.5 weight percent of a non-ionic detergent is included with the sample. Various polyoxyalkylene compounds may be employed of from about 200 to 20,000 daltons.

Moderate, and desirably substantially constant, temperatures are normally employed for carrying out the assay. The temperatures for the assay and production of a detectable signal will generally be in the range of about 4°-50° C., more usually in the range of about 10°-25° C., and frequently will be ambient temperatures, that is, about 15°-25° C.

The concentration in the aqueous test solution of analyte that may be assayed will generally vary from about $10^{-4}$ to about $10^{-15}$M, more usually from about $10^{-6}$ to $10^{-14}$M. Consideration, such as the concentration of the analyte of interest and the protocol will normally determine the concentration of the other reagents.

While the concentrations of many of the various reagents in the sample and reagent solutions will generally be determined by the concentration range of interest of the analyte, the final concentration of each of the reagents will normally be determined empirically to optimize the sensitivity of the assay over the range of interest. With certain protocols, individual reagents may be used in substantial excess without detrimentally affecting the sensitivity of the assay.

The self-contained liquid reagents can be confined in a container according to standard techniques. An important consideration is that the confinement not have a detrimental effect on the reagents confined. Exemplary of such confinement is encapsulation in a capsule.

Where the bibulous material is a strip, the size of strip 18 is dependent on several considerations. The primary consideration is to move a sufficient amount of one or more sbp members to an immunosorbing zone when one or more of the analytes are in the test solution to give a sufficient signal so that a sensitive and accurate assay is achieved. When liquid absorbing material 20 is not included the length and thickness of the strip control the amount of solution that can pass along the strip. If the transfer of a large volume of test solution is desired, the fluid capacity of the strip above the immunosorbing zone must be sufficient to accommodate the desired volume. If liquid absorbing material 20 is used, this volume requirement is not needed. In general, when liquid absorbent material 20 is not used, the fluid retention volume will be usually greater than 20 μL, preferably at least 50-200 μL. When liquid absorbent material 20 is used, strip retention volumes as low as 2-20 μL can be used but volumes of 20-200 μL are preferable.

Thickness of the strips is not critical and will normally be 0.1-2 mm, usually 0.15-1 mm, preferably 0.2-0.7 mm. Generally, the minimum thickness is dictated by the strength of the material and the need to produce a readily detectible signal whereas the maximum width will be dictated by convenience of handling and cost of the reagents.

To permit conversation of reagents and provide for samples of limited size, the width of the strip will generally be relatively narrow, usually less than 20 mm, preferably less than 10 mm. Generally, the width of the strip will not be less than about 1.0 mm and will usually range from about 2 mm to 12 mm, preferably from about 4 mm to 8 mm.

The cross-sectional dimensions of a strip have been described in the preceding discussion in terms of a rectangle for purposes of illustration and not limitation. As mentioned above, other cross-sectional shapes such as circular, triagonal, oval, etc, fall equally within the scope of this invention. The dimensions thereof can be determined by those skilled in the art with reference to the disclosure herein.

The length of the strip will depend on (1) whether an absorbent member 20 is employed, (2) the concentration of one or more of the analytes and (3) practical considerations with respect to ease of handling of device 10 and will be about 1 cm to 40 cm, usually about 2 cm to 25 cm, preferably about 4 to 20 cm but may be of any practical length. The structure of the strip can be varied widely and includes fine, medium fine, medium, medium coarse and coarse. In general, smaller pore size and finer material will provide slow capillary flow and efficient capture of bound conjugate on the strip. Courser more porous materials provide faster flow, but the efficiency of capture is reduced. Selection of the porosity of the material depends on the rate of binding of the components for a given assay.

Absorbent member 20 may be comprised of the same or different bibulous material as strip 18. Member 20 can be in the form of a strip, pad, cylinder, or other convenient shape. The dimensions of member 20 are dependent on some of the same factors as the dimensions for strip 18. The primary consideration is that member 20 be capable of absorbing the minimum volume of liquid required in the assay including the solvent for the sample, assay reagents, and any wash solutions as necessary. The dimensions of device 10 will usually be about 2-30 cm long, preferably 4-15 cm. The cross-section of the device will usually be rectangular but may be elipsoid or some other shape but will usually be flat on at least one side. The minimum and maximum cross-sectional dimensions will be 0.5 to 5 cm, preferably 1.0 to 3 cm, but may be larger when the elements of more than one device are included on a single unit.

The position of the immunosorbing zone or zones with respect to opening 44, self-contained liquid reagents 30, and absorbent material 20 is governed by the basic principle of the particular assay being employed and to which the device of the present invention is adopted. The minimum distance from the contact portion is determined by the capacity of the intervening bibulous material to non-diffusively bind the second sbp members. Desirably, the immunosorbing zone 58 (FIG. 4) should be at least 5 mm, preferably at least 10 mm, from the contact portion opposite opening 44. It may be positioned any greater distance away provided the test solution can pass thereto by capillary action. In this way, the immunoassay zone is "separated" from such contact portion. This contact portion will lie between the liquid uptake end of the strip and the absorbent material 20.

The self-contained reagents, which are normally sbp members, members of the signal producing system or wash solutions if necessary, can vary widely in concentration depending upon the particular assay protocol and their role in signal production. The amounts of sbp members are selected based on the predetermined minimum detectible amounts of the analytes that are in the test solution. The amount of each of the sbp members that contacts the immunosorbing zone will preferably equal or exceed the amount of the corresponding analyte in the test solution that contacts the immunosorbing zone. However, the amount of the sbp member may be 100 or more times lower than the corresponding amount of analyte that contacts the immunosorbing zone.

One or more sbp members and members of the signal producing system may be substantially uniformly bound to an immunosorbing zone on the strip. The amount of each sbp member and member of the signal producing system bound is dependent on the particular assay protocol employed.

In carrying out an assay utilizing the present device, the protocol will normally involve combining in an aqueous medium the sample suspected of containing the analytes and other reagents as necessary for the assay protocol chosen to form the aqueous test solution. In some instances the test solution will be the sample itself. The sample may be derived from a wide variety of sources, such as physiologic fluids, illustrated by saliva, blood, serum, plasma, urine, ocular lens fluid, spinal fluid, etc., food products such as milk and wine, chemical processing streams, food waste water, etc.

Referring now to FIGS. 1-5, the test solution is introduced into device 10 through means 44 to contact a portion of strip 18. The test solution is drawn along strip 18 through the contact portion by capillary action. Next, means 38 is depressed to break container 32 and release self-contained liquid assay reagents 30 into recess 34. Reagents 30 contact the end portion of strip 18 and begin to traverse strip 18. As mentioned above, the contact portion can also serve as the immunosorbing zone or separate immunosorbing zones can be utilized depending on the particular assay protocol chosen. Wetting of the strip by capillary action usually is allowed to continue, so that a sufficient amount of assay reagents passes through, or become bound in, as the case may be, the immunosorbing zone.

For the most part, relatively short times are involved for the solutions to traverse the strip. Usually, the traverse of the solutions over the strip will take at least 30 sec and not more than 1 hour, more usually from about 1 min to 30 min. When an enzyme is used in the signal producing means, the development of the signal will generally range from 30 sec to 30 min, more usually from about 30 sec. to 5 min.

After the liquid has traversed the strip, the immunosorbing zone is examined through means 14 for the presence of a detectible signal. Where chemical agents form part of the signal producing means that includes the label, an additional breakable container containing these reagents in a developer solution can be included in device 10 in the same or separate recess from that for container 32. The contents of this container can be released at the appropriate time by breaking the container. The liquid receiving end portion of the strip thereby comes in contact with the developer solution, which is allowed to wick along the strip to the immunosorbing zone.

When an enzyme is used as a label, the substrate will normally be in a sufficient concentration in the developer solution so as not to be rate limiting (greater concentration than Km). The developer solution will usually be appropriately buffered for the enzyme system.

A sufficient time is allowed to elapse prior to measuring the signal to produce an amount of the signal producing compound. Once opportunity has been given for production of a detectable signal, it is known whether or not at least one of the analytes in the sample is present at or above a predetermined minimum detectible amount.

The strip can be coated with a wide variety of materials to provide for enhanced properties. Coatings may include protein coatings, polysaccharide coatings, synthetic polymers, sugars or the like, which are used particularly to enhance the stability of the materials conjugated to the strip. These compounds can also be used for improved binding of the materials, such as antibody binding or the like.

The strip can be activated with reactive functionalities to provide for covalent bonding of the organic materials to be conjugated to the strip such as those described in U.S. Pat. No. 4,168,146, the relevant disclosure of which is incorporated herein by reference.

Sbp members and, where desired, members of the signal producing system, can be bound to the piece of bibulous material or strip by adsorption, rather than covalent bonding. Such binding can be non-diffusive or diffusive depending on whether or not the assay protocol requires movement of such member along the strip. This will involve contacting the bibulous material with a solution containing the materials to be bound to the strip and allowing the strip to dry. When the binding is non-diffusive, subsequent treatment with proteins, detergents, polysaccharides, or other materials capable of blocking non-specific binding sites may be required.

The device of the invention can be utilized in a wide variety of assay methods and protocols. The following examples are provided by way of illustration and not limitation. U.S. Pat. No. 4,366,241, which is incorporated herein by reference, describes an assay method for the determination of sbp members. The device has an immunosorbing zone to which an sbp member is fixed against diffusive movement. The immunosorbing zone generally lies opposite to the entry for the sample solution. In liquid-receiving relationship, with the immunosorbing zone is a liquid absorbing zone.

Employed in the method in conjunction with the device is a signal producing system which has a signal label member conjugated to an sbp member in an aqueous medium contained in a breakable capsule. The immunosorbing zone may include one or more members of the signal producing system which are bound to the zone in a manner to permit or inhibit diffusive movement of the signal producing system component. In accordance with the method protocol, the amount of signal label bound in a detection zone in the immunosorbing zone is related to the amount of analyte in the sample.

The method involves contacting the assay device with the liquid sample to which may have been added one or more components of the signal producing system. One or more solutions in corresponding breakable containers in accordance with the present invention can be employed. Such self-contained liquid reagents can be any remaining components of the signal producing system and can further serve to wash the immunosorbing zone free of non-specifically bound signal label. The signal producing system provides for a detectible signal in the immunosorbing zone which can be compared to a signal level based on a standard having a known amount of analyte or based on comparison with a portion of the bibulous material other than the immunosorbing zone.

One specific embodiment of the method of U.S. Pat. No. 4,366,241 is described in U.S. Pat. No. 4,632,901. The latter patent discloses an apparatus and process for conducting immunoassays. The apparatus comprises a first member which is a membrane or a filter to which is bound an antibody, typically a monoclonal antibody. Such membrane with antibody corresponds to an immunosorbing zone. The method further employs a second member which is composed of absorbent material which acts when in contact with the first member of induce flow (through the first member when a fluid sample is added to it. The immunoassay is conducted by applying a sample through means 44 to the upper surface of the first member to bind, e.g., antigen in the sample by means of antibody fixed to the first member. Addition of the sample is followed by addition of labeled antibody against the antigen being assayed followed by a washing step to remove unbound labeled antibody. The labeled antibody solution and the wash solution can be contained in breakable capsules in accordance with the present invention. The presence of labeled antibody on the first member after washing is indicative of the presence of the antigen in the sample being assayed.

Another example of an assay method in which the present device can be utilized is described in U.S. patent application Ser. No. 701,464, filed Feb. 14, 1985. The method is for determining the presence of an analyte in a sample suspected of containing the analyte. The method involves contacting a test solution containing the sample and a first sbp member with a portion of a strip of bibulous material capable of being traversed by the test solution through capillary action. The first sbp member is capable of binding the analyte. The strip contains a second sbp member integral therewith for concentrating and non-diffusively binding the first sbp member at a small situs or immunosorbing zone on the strip separated from the contact portion of the strip. A detectible signal is produced in relation to the presence of the analyte in the test solution. The test solution passes through the immunosorbing zone as the test solution traverses the bibulous material. After the test solution has been allowed to traverse at least a portion of the strip, the strip is contacted with a developer solution containing members of a signal producing system. Such developer solution can be contained in a capsule in the device of the invention. The contents can be released by breaking the capsule. If necessary, the strip can then be contacted with any remaining members of the signal producing system by breaking another capsule containing such members in solution. The detectible signal produced at the immunosorbing zone is then compared with the signal detectible at a portion of the strip other than the immunosorbing zone to determine the analyte in the sample. The signal produced at the immunosorbing zone can have a sharp-edged distinctive pattern that provides a sharp contrast to the signal produced at adjacent sites on the strip when analyte is present in the test solution.

A further example of an assay method in which the present device can be employed is described in U.S. patent application Ser. No. 904,595, filed Sep. 5, 1986. Such a method is directed to determining the presence of an analyte in a sample suspected of containing the analyte. The method involves contacting a test solution containing the sample, an antibody for the analyte, and a conjugate of the analyte and a label with a contact portion of a piece of bibulous material capable of being traversed in at least one direction by the test solution through capillary action. The bibulous material contains an immunosorbing zone having a first receptor capable of binding to the conjugate non-diffusively bound on the bibulous material separate from the contact portion. The bibulous material further contains a second receptor capable of binding the antibody to the analyte between the immunosorbing zone and the contact portion. The second receptor is non-diffusively bound to the bibulous material. At least a portion of the test solution is allowed to traverse the bibulous material by capillary action and thereby contact the immunosorbing zone. The zone is examined for the presence of the conjugate. To this end, the strip can be exposed to a signal producing means capable of interacting with the label to produce a signal in relation to the amount of analyte in the test solution. The signal producing means can be contained in a breakable capsule in a device of the present invention. When the capsule is broken, the signal producing means is released to contact the strip. The signal produced at the immunosorbing zone is then detected.

Another example of an assay in which the present device can be employed is disclosed in U.S. patent application Ser. No. 928,233, filed Nov. 7, 1986. In the method the presence of a predetermined minimum detectible amount of one or more analytes in a sample suspected of containing the analyte is determined. Each analyte is an sbp member. The method comprises contacting with a test solution containing the sample and predetermined amount of two or more of a plurality of first sbp members, each respectively analogous to one of the analytes, a contact portion of a piece of bibulous material capable of being traversed in at least one direction by the test solution by capillary migration. The bibulous material contains predetermined amounts of two or more of a plurality of second sbp members, each respectively capable of binding one of the analytes and corresponding first sbp member. The second sbp members are non-diffusively bound to the bibulous material at least between the contact portion and a predetermined site or immunosorbing zone on the piece of bibulous material separated from the contact portion such that in the presence of a predetermined amount of one or more analytes the analogous first sbp member migrates at least to the predetermined site on the piece of bibulous material. Next, at least a portion of the test solution is allowed to traverse the bibulous material by means of capillary migration. The predetermined site is examined for the presence of one or more of the first sbp members, which is usually indicated by the presence of a detectible signal. The predetermined site can be exposed to a signal producing means capable of interacting with the first sbp members to produce a detectible signal at the predetermined site in relation to the amount of one or more of the analytes in the sample. Such signal producing means can be contained in a breakable capsule in the device of the invention and released, upon breaking of the capsule, to contact the bibulous material.

Another example of an assay technique in which the present device finds use is described in U.S. patent application Ser. No. 928,771, filed Nov. 7, 1986. In this method the presence of an analyte in a sample suspected of containing the analyte is determined. The analyte is an sbp member. The method comprises contacting, with a test solution containing the sample and a first sbp member analogous to the analyte, a contact portion of a piece of bibulous material capable of being traversed in at least one direction by the test solution by capillary migration. The bibulous material contains a second sbp member capable of binding the analyte and the first sbp member. The second sbp member is non-diffusively bound to the bibulous material at least at a portion thereof between the contact portion and a small situs or immunosorbing zone on the piece separated from the contact portion. The surface area of the situs is substantially less than that of the piece of bibulous material. The situs is capable of binding the first sbp member not bound to said second sbp member. Next, at least a portion of the test solution is allowed to traverse the bibulous material by means of capillary migration and thereby contact the situs. The situs is examined for the presence of the first sbp member at the situs, which is usually indicated by the presence of a detectible signal. Such signal can be generated by exposing the situs to a signal producing means capable of interacting with the first sbp member to produce a detectible signal at the situs in relation to the amount of analyte in the sample. The signal producing means can be present in the device of the invention in a liquid medium in a breakable capsule. The capsule is broken to release its contents, which traverse the bibulous material through the situs by capillary action. The signal at the situs is distinguishable from signal detectible at portions of the bibulous material other than the situs.

Still another example of an assay method in which the present device can be employed is described in U.S. Pat. No. 4,552,839 and a variant thereof in U.S. Pat. No. 4,623,461. U.S. Pat. No. 4,552,839 discloses methods and compositions for determining the presence of analyte in a prticle containing medium, where the analyte of interest may be bound or unbound to a particle in a sample. By contacting the assay medium with a bibulous material at a liquid air interface, a small situs, usually a thin band or concentrated point, of particles can be obtained adjacent the interface, which site provides a signal which can be related to the presence of analyte in the sample. The particles include synthetic particles, cells, and immune complex aggregates. The size and nature of the particles, as well as the nature of the aqueous medium, can be used to modulate the formation of the small site. In some embodiments of this method one or more members of a signal producing system in a liquid medium are next contacted with the bibulous material. Such liquid medium can be contained in a breakable capsule in a device in accordance with the present invention.

In one specific embodiment of this invention antibodies to a protein, for example, human chorionic gonadotropin (HCG), are non-diffusively bound to a situs that can be observed through means 14 of FIG. 2. Enzyme labeled antibodies to HCG are diffusively deposited on strip 18 opposite sample addition means 44 or between means 44 and means 14. A breakable container containing water is in cavity 34. Substrate for the enzyme and buffer are in the water or are present in dry form on strip 18 or in cavity 34. The method is performed by applying a urine or serum sample suspected of containing HCG to strip 18 through means 44, breaking the container with means 38, waiting for liquid to be transferred past means 14, and observing the formation of an enzyme product at the situs in relation to the presence of the protein.

As a matter of convenience, the present device can be provided in a kit in packaged combination with reagents in predetermined amounts for use in assaying for an analyte. Depending on the particular assay involved, the reagents can include enzyme labeled sbp member, substrate for the enzyme, buffers, any additional substrates and cofactors required by the enzymes, dye precursor, and the like. In addition, other additives may be included, such as stabilizers, buffers, and the like. The relative amounts of the various reagents may be varied widely, to provide for concentrations in solution of the reagents which substantially optimize the sensitivity of the assay. Where appropriate, the device of the present invention can be packaged in an air-tight package in order to maintain the activity of any immunochemical agents.

Although the foregoing invention has been described in some detail by way of illustration and example for the purposes of clarity and understanding, it will be obvious that certain changes or modifications may be practiced within the scope of the appended claims.

The patents and patent applications referred to in the above description are each incorporated herein by reference in their entirety.

What is claimed is:

1. A device for conducting an assay method, said device comprising:
    (a) a housing,
    (b) means enclosed in said housing for capturing a member of a specific binding pair in a zone and for allowing liquid to be transported by capillary action away from said zone,
    (c) one or more liquid reagents releasably contained in said housing for subsequent use in conducting an assay method for the determination of an analyte in a sample, and
    (d) means in said housing for introducing the sample into the device.

2. The device of claim 1 wherein the means in (b) comprises a bibulous material that is immunosorbing or is capable of being rendered immunosorbing.

3. The device of claim 1 wherein said means in (b) comprises bibulous material having a member of a specific binding pair (sbp) bound thereto.

4. The device of claim 3 wherein said sbp member is an antibody or an antigen.

5. The device of claim 2 wherein a second piece of bibulous material is in liquid receiving relationship with said bibulous material.

6. The device of claim 5 wherein said bibulous material is a cellulose material.

7. The device of claim 1 wherein said liquid reagent or reagents are contained in a water insoluble container.

8. The device of claim 1 wherein said means in (b) is a bibulous material capable of entrapping beads coated with an sbp member.

9. The device of claim 1 wherein one or more of said liquid reagents are aqueous.

10. The device of claim 1 wherein one or more of said liquid reagents contain members of a signal producing system capable of generating a signal in relation to the amount of an analyte in the sample.

11. The device of claim 2 wherein said bibulous material has in contact with it a dry water soluble sbp member conjugated to a label.

12. The device of claim 11 wherein said label is selected from the group consisting of catalysts, enzymes, chromogens, radioactive substances, dispersible particles, and solid supports.

13. The device of claim 1 wherein said means in (d) is an opening in said device.

14. The device of claim 13 wherein said opening is adjacent to an immunosorbing zone.

15. The device of claim 2 wherein said bibulous material is a strip.

16. The device of claim 15 wherein said means for capturing a member of an sbp is a complementary sbp non-diffusively bound to said zone of said bibulous material.

17. The device of claim 1 which further comprises means for releasing said confined liquid reagent.

18. A device for conducting an assay method, said device comprising:
  (a) a housing,
  (b) bibulous material enclosed in said housing for capturing a member of a specific binding pair in a zone and for allowing liquid to be transporting by capillary action away from said zone,
  (c) one or more liquid reagents releasably contained in said housing for subsequently being rendered capable of traversing said bibulous material in conducting an assay method for the determination of an analyte in a sample, and
  (d) means in said housing for introducing the sample into the device.

19. The device of claim 18 wherein said bibulous material has a member of a specific binding pair (sbp) bound thereto.

20. The device of claim 19 wherein said sbp member is an antibody or an antigen.

21. The device of claim 18 wherein a second piece of bibulous material is in liquid receiving relationship with said bibulous material.

22. The device of claim 18 wherein said bibulous material is a cellulose material.

23. The device of claim 18 wherein said liquid reagent or reagents are contained in a container within said housing.

24. The device of claim 18 wherein said means in (b) is a bibulous material capable of entrapping beads coated with an sbp member.

25. The device of claim 18 wherein one or more of said liquid reagents are aqueous.

26. The device of claim 18 wherein one or more of said liquid reagents contain members of a signal producing system capable of generating a signal in relation to the amount of an analyte in the sample.

27. The device of claim 18 wherein said bibulous material has in contact with it a dry water soluble sbp member conjugated to a label.

28. The device of claim 27 wherein said label is selected from the group consisting of catalysts, enzymes, chromogens, radioactive substances, dispersible particles, and solid supports.

29. The device of claim 18 wherein said means in (d) is an opening in said device.

30. The device of claim 29 wherein said opening is adjacent to an immunosorbing zone.

31. The device of claim 18 wherein said bibulous material is a strip.

32. The device of claim 19 wherein said means for capturing a member of an sbp is a complementary sbp non-diffusively bound to said zone of said bibulous material.

33. The device of claim 23 which further comprises means for releasing said liquid reagent from said container.

34. A method for conducting an assay for an analyte in a sample suspected of containing said analyte, which method comprises:

(a) introducing a test solution comprising said sample into the device of claim 35 through said means of (d),
  (b) allowing said test solution to traverse at least a portion of said bibulous material,
  (c) releasing said liquid reagent to allow said liquid reagent to traverse at least a portion of said bibulous material, and
  (d) observing said bibulous material for the presence of a signal in relation to the presence of analyte in said sample.

35. A method for conducting an assay for an analyte in a sample suspected of containing said analyte, which method comprises:
  (a) introducing a test solution comprising said sample into the device of claim 1 through said means of (d),
  (b) allowing said test solution to traverse at least a portion of said bibulous material,
  (c) releasing said liquid reagent to allow said liquid reagent to traverse at least a portion of said bibulous material, and
  (d) observing said bibulous material for the presence of a signal in relation to the presence of analyte in said sample.

36. A device for conducting an assay method, said device comprising:
  (a) a housing,
  (b) bibulous material enclosed in said housing, said bibulous material having a component of a signal producing system bound thereto and a liquid contacting portion, said bibulous material being capable of allowing liquid to be transported by capillary action away from said liquid contacting portion,
  (c) one or more liquid reagents confined for subsequent release in at least one breakable container enclosed in said housing, said container being separate from or integral with said housing, and
  (d) means in said housing for introducing a sample into the device.

37. The device of claim 36 wherein said bibulous material is immunosorbing.

38. The device of claim 36 wherein said component of said signal producing system is a member of a specific binding pair (sbp).

39. The device of claim 38 wherein said sbp member is an antibody or an antigen.

40. The device of claim 36 wherein a second piece of bibulous material is in liquid receiving relationship with said bibulous material.

41. The device of claim 36 wherein said bibulous material is a cellulose material.

42. The device of claim 36 wherein said liquid reagent or reagents are contained in a water insoluble breakable container.

43. The device of claim 36 wherein said liquid reagent or reagents are contained in a container that is integral with said housing, said container having a breakable seal.

44. The device of claim 36 wherein one or more of said liquid reagents are aqueous.

45. The device of claim 36 wherein one or more of said liquid reagents contain other members of said signal producing system capable of generating a signal in relation to the amount of an analyte in the sample.

46. The device of claim 36 wherein said component of said signal producing system is a dry water soluble sbp member conjugated to a label.

47. The device of claim 46 wherein said label is selected from the group consisting of catalysts, enzymes, chromogens, radioactive substances, dispersible particles, and solid supports.

48. The device of claim 36 wherein said means in (d) is an opening in said device.

49. The device of claim 48 wherein said opening is adjacent to an immunosorbing zone.

50. The device of claim 36 wherein said bibulous material is a strip.

51. The device of claim 50 wherein said component of a signal producing system is an sbp member non-diffusively bound in a zone of said bibulous material.

52. The device of claim 36 which further comprises means for releasing said confined liquid reagent.

53. A device for conducting an assay method, said device comprising:
   (a) a housing,
   (b) bibulous material enclosed in said housing, said bibulous material having a component of a signal producing system bound thereto and a contact portion and being capable of allowing liquid to be transported by capillary action away from said contact portion,
   (c) one or more liquid reagents releasably contained in said housing for subsequently being rendered capable of traversing said bibulous material in conducting an assay method for the determination of an analyte in a sample, and
   (d) means in said housing for introducing the sample into the device.

54. The device of claim 53 wherein said component of said signal producing system is a member of a specific binding pair (sbp).

55. The device of claim 54 wherein said sbp member is an antibody or an antigen.

56. The device of claim 53 wherein a second piece of bibulous material is in liquid receiving relationship with said bibulous material.

57. The device of claim 53 wherein said bibulous material is a cellulose material.

58. The device of claim 53 wherein said liquid reagent or reagents are contained in a breakable container within said housing.

59. The device of claim 53 wherein said liquid reagent or reagents are contained in a container that is integral with said housing, said container having a breakable seal.

60. The device of claim 53 wherein one or more of said liquid reagents are aqueous.

61. The device of claim 53 wherein one or more of said liquid reagents contain other members of said signal producing system capable of generating a signal in relation to the amount of an analyte in the sample.

62. The device of claim 53 wherein said component of said signal producing system is a dry water soluble sbp member conjugated to a label.

63. The device of claim 62 wherein said label is selected from the group consisting of catalysts, enzymes, chromogens, radioactive substances, dispersible particles, and solid supports.

64. The device of claim 53 wherein said means in (d) is an opening in said device.

65. The device of claim 64 wherein said opening is adjacent to an immunosorbing zone.

66. The device of claim 53 wherein said bibulous material is a strip.

67. The device of claim 64 wherein said component of said signal producing system is an sbp member non-diffusively bound in a zone on said bibulous material.

68. The device of claim 58 which further comprises means for releasing said liquid reagent from said container.

69. A method for conducting an assay for an analyte in a sample suspected of containing said analyte, which method comprises:
   (a) introducing a test solution comprising said analyte into the device of claim 36 through said means of (d)
   (b) allowing said test solution to traverse at least a portion of said bibulous material,
   (c) breaking said breakable container to allow said liquid reagent to traverse at least a portion of said bibulous material, and
   (d) observing said bibulous material for the presence of a signal in relation to the presence of analyte in said sample.

70. A method for conducting an assay for an analyte in a sample suspected of containing said analyte, which method comprises:
   (a) introducing a test solution comprising said analyte into the device of claim 53 through said means of (d),
   (b) allowing said test solution to traverse at least a portion of said bibulous material,
   (c) releasing said liquid reagent to allow said liquid reagent to traverse at least a portion of said bibulous material, and
   (d) observing said bibulous material for the presence of a signal in relation to the presence of analyte in said sample.

* * * * *